United States Patent
Angibaud et al.

(10) Patent No.: US 7,408,063 B2
(45) Date of Patent: Aug. 5, 2008

(54) 1,8-ANNELATED QUINOLINE DERIVATIVES SUBSTITUTED WITH CARBON-LINKED TRIAZOLES AS FARNESYL TRANSFERASE INHIBITORS

(75) Inventors: Patrick René Angibaud, Fontaine-Bellenger (FR); Marc Gaston Venet, Le Mesnil Esnard (FR)

(73) Assignee: Janssen Pharmaceutica, N.V., Beerse (BE)

( * ) Notice: Subject to any disclaimer, the term of this patent is extended or adjusted under 35 U.S.C. 154(b) by 568 days.

(21) Appl. No.: 10/498,535

(22) PCT Filed: Dec. 11, 2002

(86) PCT No.: PCT/EP02/14089

§ 371 (c)(1),
(2), (4) Date: Jun. 14, 2004

(87) PCT Pub. No.: WO03/051880

PCT Pub. Date: Jun. 26, 2003

(65) Prior Publication Data

US 2005/0176702 A1    Aug. 11, 2005

(30) Foreign Application Priority Data

Dec. 19, 2001   (EP) ................... 01204989

(51) Int. Cl.
C07D 413/04 (2006.01)
C07D 471/06 (2006.01)
C07D 487/06 (2006.01)
A61K 31/4355 (2006.01)
A61K 31/435 (2006.01)

(52) U.S. Cl. ............... 546/80; 546/79; 514/290

(58) Field of Classification Search .......... 546/79, 546/80, 70; 514/290
See application file for complete search history.

(56) References Cited

FOREIGN PATENT DOCUMENTS

| WO | WO 97/16443 A1 | 5/1997 |
|---|---|---|
| WO | WO 97/21701 A1 | 6/1997 |
| WO | WO 98/40383 A1 | 9/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |

OTHER PUBLICATIONS

Dorwald F. A. Side Reactions in Organic Synthesis, 2005, Wiley: VCH, Weinheim p. IX of Preface.*
Kohl et al., *Science*, vol. 260, 1934-1937, 1993.
Rak. J. et al, *Cancer Research*, 55, 4575-4580, 1995.
Finney, D.J., Probit Analyses, 2nd Ed. Chapter 10, Graded Responses, Cambridge Univerity Press, Cambridge 1962).

* cited by examiner

*Primary Examiner*—Rita J Desai

(57) ABSTRACT

This invention comprises the novel compounds of formula (I)

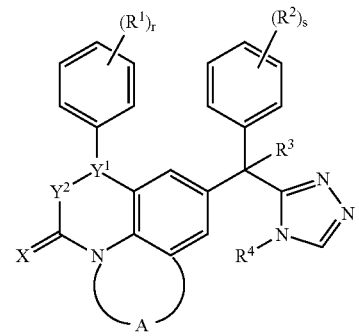

wherein r, s, A, X, $Y^1$, $Y^2$, $R^1$, $R^2$, $R^3$, and $R^4$ have defined meanings, having farnesyl transferase inhibiting activity; their preparation, compositions containing them and their use as a medicine.

5 Claims, No Drawings

1,8-ANNELATED QUINOLINE DERIVATIVES SUBSTITUTED WITH CARBON-LINKED TRIAZOLES AS FARNESYL TRANSFERASE INHIBITORS

CROSS REFERENCE TO RELATED APPLICATIONS

This application is the national stage of Application No. PCT/EP02/14089, filed Dec. 11, 2002, which application claims priority from EP 01204989.6 filed Dec. 19, 2001.

The present invention is concerned with novel 1,8-annelated quinoline derivatives substituted with carbon-linked triazoles, the preparation thereof, pharmaceutical compositions comprising said novel compounds and the use of these compounds as a medicine as well as methods of treatment by administering said compounds.

Oncogenes frequently encode protein components of signal transduction pathways, which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes are frequently associated with human cancer. A particular group of oncogenes is known as ras, which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumour cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyse this modification, i.e. farnesyl transferase, will prevent the membrane attachment of $p21^{ras}$ and block the aberrant growth of ras-transformed tumours. Hence, it is generally accepted in the art that farnesyl transferase inhibitors can be very useful as anticancer agents for tumours in which ras contributes to transformation.

Since mutated oncogenic forms of ras are frequently found in many human cancers, most notably in more than 50% of colon and pancreatic carcinomas (Kohl et al., Science, vol 260, 1834-1837, 1993), it has been suggested that farnesyl tranferase inhibitors can be very useful against these types of cancer.

In EP-0,371,564 there are described (1H-azol-1-ylmethyl) substituted quinoline and quinolinone derivatives, which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolinone derivatives, which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolinone compounds having farnesyl transferase inhibiting activity are described in WO 00/12498, 00/12499, 00/47574 and 01/53289.

Unexpectedly, it has been found that the present novel compounds, all having a phenyl substituent on the 4-position of the 1,8-annelated quinolinone moiety bearing a carbon-linked triazole, show farnesyl protein transferase inhibiting activity. The present compounds may have advantage properties with regard to solubility and stability.

SUMMARY OF THE INVENTION

The present invention concerns compounds of formula (I):

(I)

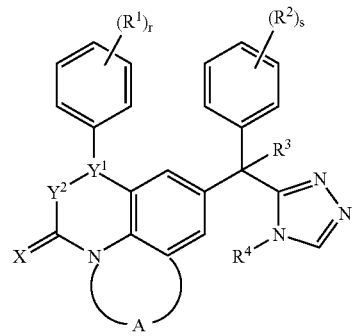

or a pharmaceutically acceptable salt or N-oxide or stereochemically isomeric form thereof, wherein
r and s are each independently 1, 2 or 3;
X is oxygen or sulfur;
-A- is a bivalent radical of formula

| —CH═CH— | (a-1) |
|---|---|
| —CH$_2$—CH$_2$— | (a-2) |
| —CH$_2$—CH$_2$—CH$_2$— | (a-3) |
| —CH$_2$—O— | (a-4) or |
| —CH$_2$—CH$_2$—O— | (a-5) | wherein optionally one hydrogen atom may be replaced by $C_{1-4}$alkyl;
$>Y^1$—$Y^2$— is a trivalent radical of formula

| $>C$═$CR^5$— | (y-1) or |
|---|---|
| $>CH$—$CHR^5$— | (y-2), | wherein $R^5$ is hydrogen, halo or $C_{1-6}$alkyl;
$R^1$ is hydrogen, hydroxy, halo, cyano, nitro, $C_{1-6}$alkyl, —(CR$^{12}$R$^{13}$)$_p$-C$_{3-10}$cycloalkyl, cyanoC$_{1-6}$alkyl, hydroxyC$_{1-6}$alkyl, C$_{1-6}$alkyloxyC$_{1-6}$alkyl, trihalomethyl, -C$_{1-6}$alkyl-NR$^{14}$R$^{15}$, C$_{1-6}$alkyloxy, hydroxyC$_{1-6}$alkyloxy, trihalomethoxy, C$_{2-6}$alkenyl, C$_{2-6}$alkynyl, —CHO, C$_{1-6}$alkylcarbonyl, hydroxycarbonyl, C$_{1-6}$alkyloxycarbonyl, —CONR$^{14}$R$^{15}$, —CONR$^{14}$—O—C$_{1-6}$alkyl, —CONR$^{14}$-C$_{1-6}$alkenyl, —OC(O)R$^{16}$, —CR$^{16}$═NR$^{17}$ or —CR$^{16}$═N—OR$^{17}$;
p is 0, or 2;
$R^{12}$ and $R^{13}$ are independently hydrogen or $C_{1-6}$ alkyl and are independently defined for each iteration of p in excess of 1;
$R^{14}$ and $R^{15}$ are independently hydrogen, $C_{1-6}$ alkyl or —(CR$^{12}$R$^{13}$)$_p$-C$_{3-10}$cycloalkyl;
two $R^1$ substituents adjacent to one another on the phenyl ring may form together a bivalent radical of formula

| —O—CH$_2$—O— | (b-1) |
|---|---|
| —O—CH$_2$—CH$_2$—O— | (b-2) |
| —O—CH═CH— | (b-3) or |
| —O—CH$_2$—CH$_2$— | (b-4); |

$R^{16}$ and $R^{17}$ are independently hydrogen, $C_{1-6}$ alkyl or $-(CR^{12}R^{13})_p-C_{3-10}$cycloalkyl;

$R^2$ is hydrogen, hydroxy, halo, cyano, nitro, $C_{1-6}$alkyl, $C_{1-6}$alkyloxy, trihalomethyl, $C_{1-6}$alkylthio, di($C_{1-6}$alkyl)amino, -$C_{1-6}$alkyl-$NR^{14}R^{15}$, trihalomethoxy, $C_{2-6}$alkenyl, hydroxycarbonyl, $C_{1-6}$alkyloxycarbonyl, $-CONR^{14}R^{15}$, $-(CR^{12}R^{13})_p-C_{3-10}$cycloalkyl, cyano$C_{1-6}$alkyl, mono- or di-halo$C_{1-6}$alkyl, hydroxy$C_{1-6}$alkyl, $C_{1-6}$alkyloxy$C_{1-6}$alkyl, $R^{16}SC_{1-6}$alkyl, Het$^1C_{1-6}$alkyl, Het$^1C_{1-6}$alkyl in which the $C_{1-6}$alkyl moiety is substituted by hydroxy, Het$^1SC_{1-6}$ alkyl,
-$C_{1-6}$alkyl$NR^{14}$-$C_{1-6}$alkyloxy$C_{1-6}$alkyl, -$C_{1-6}$alkyl$NR^{14}C_{2-6}$alkenyl, -$C_{1-6}$alkyl$NR^{14}C_{2-6}$alkynyl, -$C_{1-6}$alkyl$NR^{14}C_{1-16}$alkyl-$NR^{14}R^{15}$, -$C_{1-6}$alkyl$NR^{14}C_{1-6}$alkyl-Het$^1$, -$C_{1-6}$alkyl$NR^{14}C_{1-6}$alkylC(O)OC$_{1-6}$alkyl, $C_{2-6}$alkynyl, —CHO, $C_{1-6}$alkylcarbonyl, —CONR$^{14}$-$C_{1-6}$alkyl-$NR^{14}R^{15}$, —CONR$^{14}$—O—$C_{1-6}$alkyl, —CONR$^{14}$-$C_{1-6}$alkenyl, —NR$^{14}R^{15}$, —OC(O)R$^{16}$, —CR$^{16}$=NR$^{17}$, —CR$^{16}$=N—OR or —C(NR$^{18}R^{19}$)=NR$^{20}$;

two $R^2$ substituents adjacent to one another on the phenyl ring may together form a bivalent radical of formula —O—CH$_2$—O— (b-1), —O—CH$_2$—CH$_2$—O— (b-2)

—O—CH=CH— (b-3)

—O—CH$_2$—CH$_2$— (b-4) or

—CH$_2$—O—CH$_2$ (b-5);

$R^{16}$ and $R^{17}$ are independently hydrogen, $C_{1-6}$ alkyl or $-(CR^{12}R^{13})_p-C_{3-10}$ocycloalkyl;

$R^{18}$, $R^{19}$ and $R^{20}$ are independently hydrogen and $C_{1-6}$alkyl;

$R^3$ is hydrogen, halo, $C_{1-6}$alkyl, $-(CR^{12}R^{13})_p-C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyl, $C_{1-6}$alkyloxycarbonyl$C_{1-6}$alkyl, -$C_{1-6}$alkyl-$NR^{14}R^{15}$, -$C_{1-6}$alkyl-$CONR^{14}R^{15}$, Het$^1$, or a radical of formula —O—R$^6$ (c-1)

—NR$^7R^8$ (c-2) or

—N=CR$^6R^7$ (c-3)

wherein $R^6$ is hydrogen, $C_{1-6}$alkyl, $-(CR^{12}R^{13})_p-C_{3-10}$ocycloalkyl, a group of formula —NR$^{14}R^{15}$ or -$C_{1-6}$alkylC(O)OC$_{1-6}$alkyl $NR^{14}R^{15}$, or a radical of formula -Alk-OR$^9$ or -Alk-NR$^{10}R^{11}$;

$R^7$ is hydrogen, $C_{1-6}$alkyl, $-(CR^{12}R^{13})_p-C_{3-10}$cycloalkyl;

$R^8$ is hydrogen, hydroxy, $C_{1-6}$alkyl, $-(CR^{12}R^{13})_p-C_{3-10}$cycloalkyl, $C_{1-6}$alkylcarbonylamino, $C_{1-6}$alkylcarbonyl, halo$C_{1-6}$alkylcarbonyl, Ar$^1C_{1-6}$alkylcarbonyl, Het$^1C_{1-6}$alkylcarbonyl, Ar$^1$carbonyl, $C_{1-6}$alkyloxycarbonyl, trihalo$C_{1-6}$alkyloxycarbonyl, $C_{1-6}$alkyloxy$C_{1-6}$alkylcarbonyl, aminocarbonyl, mono- or di($C_{1-6}$alkyl)aminocarbonyl wherein the alkyl moiety may optionally be substituted by one or more substituents independently selected from Ar$^1$ and $C_{1-6}$alkyloxycarbonyl substituents; aminocarbonylcarbonyl, mono- or di($C_{1-6}$alkyl)amino$C_{1-6}$alkylcarbonyl, or a radical of formula -Alk-OR$^9$ or Alk-NR$^{10}R^{11}$; wherein Alk is $C_{1-6}$alkanediyl;

$R^9$ is hydrogen, $C_{1-6}$alkyl, $-(CR^{12}R^{13})_p-C_{3-10}$cycloalkyl;

$R^{10}$ is hydrogen, $C_{1-6}$alkyl, $-(CR^{12}R^{13})_p-C_{3-10}$cycloalkyl;

$R^{11}$ is hydrogen, $C_{1-6}$alkyl, $-(CR^{12}R^{13})_p-C_{3-10}$cycloalkyl;

$R^4$ is hydrogen or $C_{1-6}$alkyl;

Ar$^1$ is phenyl, naphthyl or phenyl, or naphthyl substituted by one to five substituents each independently selected from halo, hydroxy, cyano, nitro, amino, $C_{1-6}$alkyl, halo$C_{1-6}$alkyl, -alkyl$NR^{14}R^{15}$, $C_{1-6}$alkyloxy, OCF$_3$, hydroxycarbonyl, $C_{1-6}$alkyloxycarbonyl, aryloxy, —NR$^{14}R^{15}$, $C_{1-6}$alkylsulfonylamino, oxime or phenyl, or a bivalent substituent of formula —O—CH$_2$—O— or —O—CH$_2$—CH$_2$—O—;

Het$^1$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkyl$NR^{14}R^{15}$, $C_{1-6}$alkyloxy, OCF$_3$, hydroxycarbonyl, $C_{1-6}$alkyloxycarbonyl, —CONR$^{14}R^{15}$, —NR$^{14}R^{15}$, $C_{1-6}$alkylsulfonylamino, oxime or phenyl.

aryl is phenyl, naphthalenyl, phenyl substituted with one or more substituents each independently selected from halo, $C_{1-6}$alkyl, $C_{1-6}$alkyloxy, trifluoromethyl, cyano, or hydroxycarbonyl; or naphtalenyl substituted with one or more substituents each independently selected from halo, $C_{1-6}$alkyl, $C_{1-6}$alkyloxy, trifluoromethyl, cyano or hydroxycarbonyl;

DETAILED DESCRIPTION OF THE INVENTION

As used in the foregoing definitions and hereinafter, halo is generic to fluoro, chloro, bromo and iodo; $C_{1-2}$alkyl defines methyl and ethyl; $C_{1-4}$alkyl includes $C_{1-2}$alkyl and straight and branched chain saturated hydrocarbon radicals having from 3 to 4 carbon atoms such as, e.g. propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like.

The pharmaceutically acceptable salts as mentioned hereinabove are meant to comprise the therapeutically active non-toxic acid and base addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

Compounds of formula (I) can be in the zwitterion form.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms, which said compound might possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Wherever -A- is a bivalent radical of formula (a-4) or (a-5), the CH2 moiety in said bivalent radical is preferably connected to the nitrogen atom of the 2-quinolinone-moiety of the compounds of formula (I) or the intermediates of formula (II).

Whenever used hereinafter, the term "N-imidazolyl" means that the imidazolyl is attached to the rest of the molecule through a nitrogen atom.

Whenever used hereinafter, the term "compounds of formula (I)" is meant to include also the pharmaceutically acceptable acid and base addition salts and all stereoisomeric forms.

A group of interesting compounds consists of those compounds of formula (I) wherein one or more of the following restrictions apply;
a) r and s are each independently 1
b) X is oxygen;
c) -A- is a bivalent radical of formula (a-2) or (a-3);
d) >$Y^1$—$Y^2$— is a trivalent radical of formula (y-1) wherein $R^5$ is hydrogen;
e) $R^1$ is halo, $C_{1-6}$alkyl, $C_{2-6}$alkenyl or $C_{2-6}$alkynyl;
f) $R^2$ is halo, cyano, nitro, $C_{1-6}$alkyl, cyano$C_{1-6}$alkyl, hydroxy$C_{1-6}$alkyl or $Het^1C_{1-6}$alkyl;
g) $R^3$ is hydrogen, cyano$C_{1-6}$alkyl, -$C_{1-6}$alkyl-$CONH_2$, $Het^1$ or is a radical of (c-1), (c-2), or (c-3) wherein $R^6$ is hydrogen, $R^7$ is hydrogen or $C_{1-6}$alkyl and $R^8$ is hydrogen, hydroxy or $C_{1-6}$alkyl;
h) $R^4$ is $C_{1-2}$alkyl.

Another group of interesting compounds consists of those compounds of formula (I) wherein one or more of the following restrictions apply;
a) r and s are each independently 1;
b) X is oxygen;
c) -A- is a bivalent radical of formula (a-2) or (a-3);
d) >$Y^1$—$Y^2$— is a trivalent radical of formula (y-1) wherein $R^5$ is hydrogen;
e) $R^2$ is halo, $C_{1-6}$alkyl, $C_{2-6}$alkenyl, $C_{2-6}$alkynyl or $C_{1-6}$alkyloxy;
f) $R^2$ is halo, cyano, $C_{1-6}$alkyl, cyano$C_{1-16}$alkyl, hydroxy$C_{1-6}$alkyl or $Het^1C_{1-6}$alkyl;
g) $R^3$ is hydrogen, cyano$C_{1-6}$alkyl, -$C_{1-6}$alkyl-$CONH_2$, $Het^1$ or is a radical of (c-1), (c-2), or (c-3) wherein $R^6$ is hydrogen, $R^7$ is hydrogen or $C_{1-6}$alkyl and $R^8$ is hydrogen, hydroxy or $C_{1-6}$alkyl;
h) $R^4$ is $C_{1-2}$alkyl.

A further group of interesting compounds consists of those compounds of formula (I) wherein one or more of the following restrictions apply;
a) r and s are each independently 1;
b) X is oxygen;
c) -A- is a bivalent radical of formula (a-2), (a-3) or (a-4);
d) >$Y^1$—$Y^2$— is a trivalent radical of formula (y-1) wherein $R^5$ is hydrogen or halo;
e) $R^1$ is halo;
f) $R^2$ is halo or cyano;
g) $R^3$ is hydrogen, hydroxy, amino, $C_{1-6}$alkyloxy, hydroxy $C_{1-6}$alkyloxy, $C_{1-6}$alkylcarbonylamino or N-imidazolyl;
h) $R^4$ is $C_{1-2}$alkyl.

A more interesting group of compounds consists of those compounds of formula (I) wherein one or more of the following restrictions apply;
a) $R^1$ is 3-chloro, 3-bromo, 3-methyl, or 3-ethyloxy;
b) $R^2$ is in the para-position, or 1N-1,2, 3, 4 tetrazolyl$C_{1-6}$alkyl;
c) $R^3$ is $NH_2$ or N-imidazolyl;
d) $R^4$ is methyl.

A particular group of compounds consists of those compounds of formula (I) wherein r and s are each independently 1; X is oxygen; -A- is a bivalent radical of formula (a-2); >$Y^1Y^2$- is a trivalent radical of formula (y-1) wherein $R^5$ is hydrogen; $R^1$ is halo or $C_{1-6}$alkyl; $R^2$ is halo, cyano, $C_{1-6}$alkyl or $Het^1C_{1-6}$alkyl; $R^3$ is hydrogen, hydroxy, $NH_2$ or $Het^1$; and $R^4$ is $C_{1-2}$alkyl.

A further particular group of compounds consists of those compounds of formula (I) wherein r and s are each independently 1; X is oxygen; -A- is a bivalent radical of formula (a-2); >$Y^1$—$Y^2$— is a trivalent radical of formula (y-1) wherein $R^5$ is hydrogen; $R^1$ is halo, $C_{1-6}$alkyl, or $C_{1-6}$alkyloxy; $R^2$ is halo, cyano, $C_{1-6}$alkyl or $Het^1C_{1-6}$alkyl; $R^3$ is hydrogen, hydroxy, $NH_2$ or $Het^1$; and $R^4$ is $C_{1-2}$alkyl.

Preferred compounds are those compounds of formula (I) wherein r and s are each independently 1; X is oxygen; -A- is a bivalent radical of formula (a-2), (a-3) or (a-4); >$Y^1$—$Y^2$— is a trivalent radical of formula (y-1) wherein $R^5$ is hydrogen or halo; $R^1$ is halo; $R^2$ is halo or cyano; $R^3$ is hydrogen, hydroxy, amino, $C_{1-6}$alkyloxy, hydroxy$C_{1-6}$alkyloxy, $C_{1-6}$alkylcarbonylamino or N-imidazolyl; and $R^4$ is $C_{1-2}$alkyl.

Most preferred compounds are
6-(3-chlorophenyl)-1,2-dihydro-8-[(4-iodophenyl)(4-methyl-4H-1,2,4-triazol-3-yl)methyl]-4H-pyrrolo[3,2,1-ij] quinolin-4-one;
4-[[6-(3-chlorophenyl)-1,2-dihydro-4-oxo-4H-pyrrolo[3,2,1-ij]quinolin-8-yl](4-methyl-4H-1,2,4-triazol-3-yl)methyl]- benzonitrile;
7-(3-chlorophenyl)-9-[(4-chlorophenyl)hydroxy(4-methyl-4H-1,2,4-triazol-3-yl)methyl]-2,3-dihydro-1H,5H-benzo [ij]quinolizin-5-one;
6-(3-chlorophenyl)-8-[(4-fluorophenyl)hydroxy(4-methyl-4H-1,2,4-triazol-3-yl)methyl]-1,2-dihydro-4H-pyrrolo[3,2,1-ij]quinolin-4-one;
6-(4-chlorophenyl)-8-[(4-chlorophenyl)hydroxy(4-methyl-4H-1,2,4-triazol-3-yl)methyl]-1,2-dihydro-4H-pyrrolo[3,2,1-ij]quinolin-4-one;
6-(3-bromophenyl)-8-[(4-bromophenyl)hydroxy(4-methyl-4H-1,2,4-triazol-3-yl)methyl]-1,2-dihydro-4H-pyrrolo[3,2,1-ij]quinolin-4-one;
N-[[6-(3-chlorophenyl)-1,2-dihydro-4-oxo-4H-pyrrolo[3,2,1-ij]quinolin-8-yl](4-fluorophenyl)(4-methyl-4H-1,2,4-triazol-3-yl)methyl]-acetamide;

7-(3-chlorophenyl)-9-[(4-chlorophenyl)methoxy(4-methyl-4H-1,2,4-triazol-3-yl)methyl]-2,3-dihydro-1H,5H-benzo[ij]quinolizin-5-one;

6-(3-chlorophenyl)-8-[(4-fluorophenyl)(2-hydroxyethoxy)(4-methyl-4H-1,2,4-triazol-3-yl)methyl]-1,2-dihydro-4H-pyrrolo[3,2,1-ij]quinolin-4-one;

6-(3-chlorophenyl)-8-[(4-fluorophenyl)-1 H-imidazol-1-yl(4-methyl-4H-1,2,4-triazol-3-yl)methyl]-1,2-dihydro-4H-pyrrolo[3,2,1-ij]quinolin-4-one;

8-[amino(4-fluorophenyl)(4-methyl-4H-1,2,4-triazol-3-yl)methyl]-6-(3-chlorophenyl)-1,2-dihydro-4H-pyrrolo[3,2,1-ij]quinolin-4-one and their pharmaceutically acceptable salts.

The compounds of formula (I) and their pharmaceutically acceptable salts and N-oxides and stereochemically isomeric forms thereof may be prepared, for example, by the following processes:

a) Compounds of formula (I), wherein $R^4$ is $C_{1-6}$alkyl and $R^3$ is hydroxy, said compounds being referred to as compounds of formula (I-a), may be prepared by reacting an intermediate ketone of formula (II) with an intermediate triazole reagent of formula (III-a) wherein $R^{21}$ is hydrogen or $C_{1-6}$ alkyl, to form intermediates of formula (IVa) and subsequently removing the 3-mercapto or the 3-$C_{1-6}$alkylmercapto group. More in particular, the compounds of formula (I-a) may be prepared by reacting the compound of formula (II) with the triazole reagent (III-a), preferably in a reaction-inert solvent such as tetrahydrofuran, in the presence of a strong base such as butyl lithium at a temperature ranging from −78° C. to room temperature. Removal of the 3-mercapto group is conveniently effected with sodium nitrite, for example in THF/$H_2O$ in the presence of nitric acid. Removal of, for example, the 3-methylmercapto group is conveniently effected with Raney Nickel in ethanol or acetone. Another method for obtaining intermediates of formula (IVa) starting from intermediates of formula (II) is described in the examples.

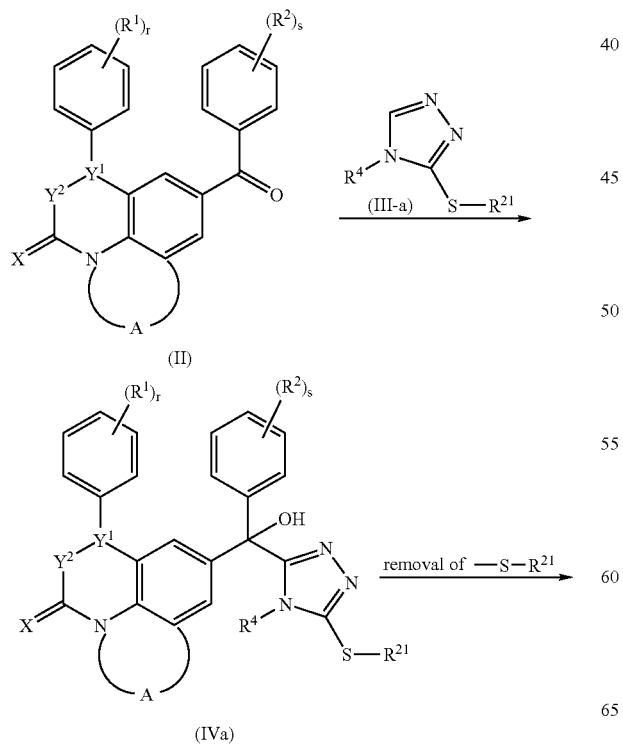

b) Compounds of formula (I), wherein $R^4$ is hydrogen and $R^3$ is hydroxy, said compounds being referred to as compounds of formula (I-b), may be prepared by reacting an intermediate ketone of formula (II) with an intermediate triazole reagent of formula (III-b) wherein P is an optional protective group such as, for example, a sulfonyl group, e.g. a dimethylamino sulfonyl group, which can be removed after the addition reaction. Said reaction requires the presence of a suitable strong base, such as, for example, butyl lithium in an appropriate solvent such as tetrahydrofuran

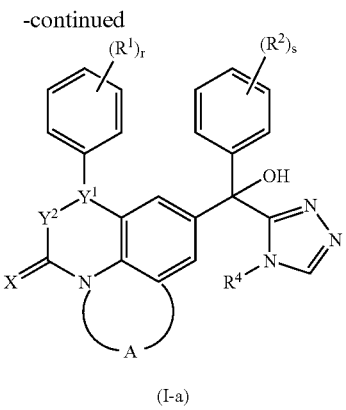

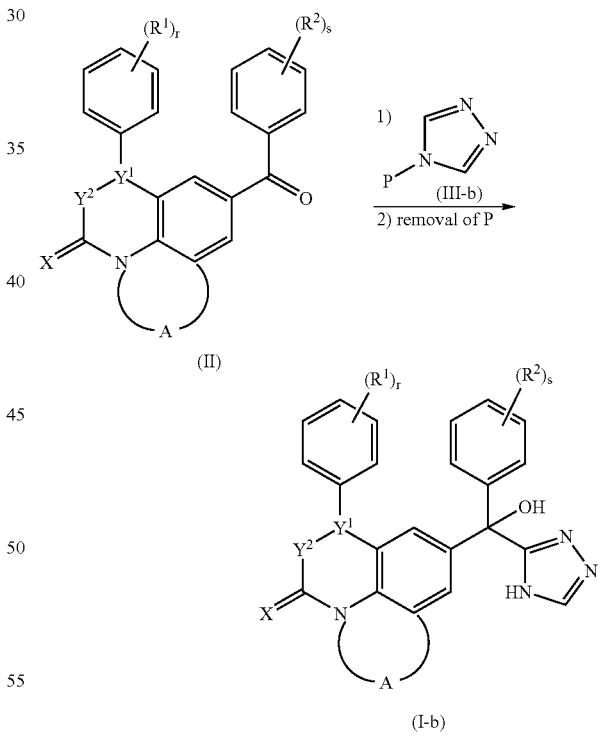

Compounds of formula (I-a) and (I-b) can optionally be the subject of one or more of the following conversions in any desired order:

(i) converting a compound of formula (I) into a different compound of formula (I);

(ii) converting a compound of formula (I) into a pharmaceutically acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

Examples of the conversion of one compound of formula (I) into a different compound of formula (I) include the following reactions:

a) Compounds of formula (I-c) wherein $R^3$ is hydroxy, can be converted into compounds of formula (I-d), defined as a compound of formula (I) wherein $R^3$ is hydrogen, by submitting the compounds of formula (I-c) to appropriate reducing conditions, such as, e.g. stirring in acetic acid in the presence of formamide, or treatment with sodium borohydride/trifluoroacetic acid.

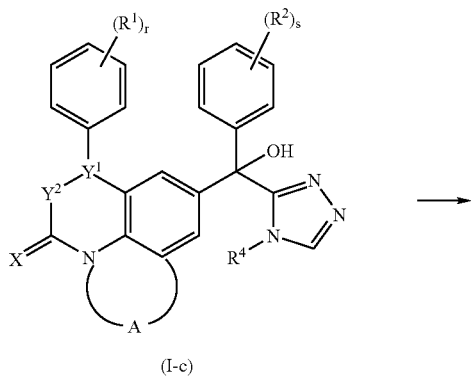

b) Compounds of formula (I-c) can be converted to compounds of formula (I-e) wherein $R^3$ is halo, by reacting the compounds of formula (I-c) with a suitable halogenating agent, such as, e.g. thionyl chloride or phosphorus tribromide. Successively, the compounds of formula (I-e) can be treated with a reagent of formula H-NR$^7$R$^8$ in a reaction-inert solvent, thereby yielding compounds of formula (I-f).

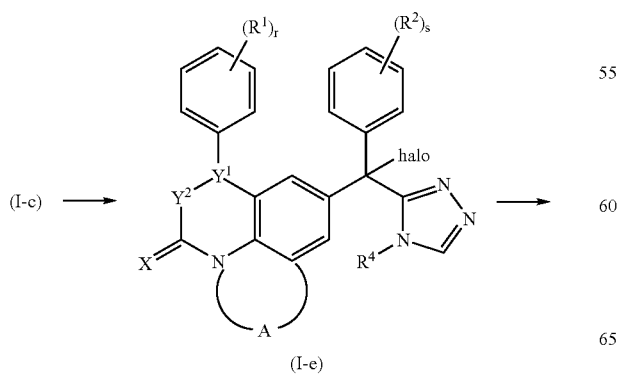

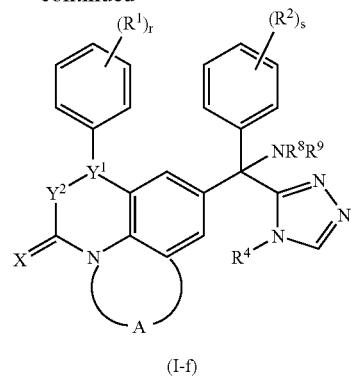

c) Compounds of formula (I-c) can be converted into compounds of formula (I-f), for example, by treatment with SOCl2, and then NH$_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.

d) A compound of formula (I-h), defined as a compound of formula (I) wherein X is sulfur, may be prepared by reacting the corresponding compound of formula (I-g), defined as a compound of formula (I) wherein X is oxygen, with a reagent like phosphorus pentasulfide or Lawesson's reagent in a suitable solvent such as, for example, pyridine.

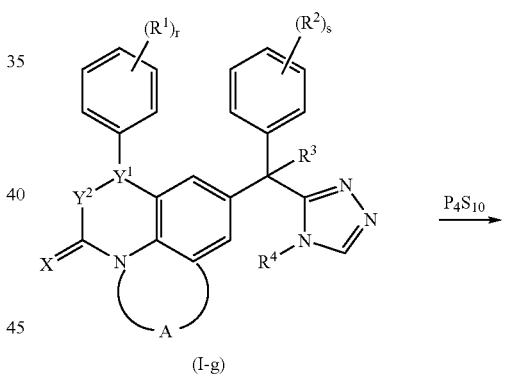

e) Compounds of formula (I) in which >Y$^1$—Y$^2$ represents a radical of formula (y-1) can be converted into corresponding compounds of formula (I) in which >Y$^1$—Y$^2$ represents a radical of formula (y-2) by conventional reduction procedures, for example, hydrogenation or reduction by treatment with sodium borohydride in a suitable solvent, e.g. methanol and vice versa by conventional oxidation procedures such as, for example, treatment with bromine in an appropriate solvent such as, e.g. bromobenzene, or treatment with iodine in the presence of acetic acid and potassium acetate. Said oxidation reaction can give rise to side-products wherein the bivalent radical -A- is oxidized. For instance, oxidation of intermediates of formula (II) in which $>Y^1-Y^2$ represents a radical of formula (y-2), wherein -A- is (a-2) may give intermediates of formula (II) in which $>Y^1-Y^2$ represents a radical of formula (y-1) wherein -A- is (a-1).

f) The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The intermediates and starting materials used in the above-described processes may be prepared in conventional manner using procedures known in the art for example as described in the above-mentioned patent specifications WO 97/16443, WO 97/21701, WO 98/40383, WO 98/49157 and WO 00/39082.

For example intermediates of formula (II) can be prepared by procedures described in International Patent Specification No. WO 98/40383, from page 11 to page 13, or by processes analogous thereto. In addition an intermediate keton of formula (II) can be prepared by reacting an intermediate compound of formula (V) with an intermediate compound of formula (VI) wherein Z represents $B(OH)_2$ or $Sn(C_{1-4}alkyl)_3$, and addition of carbon monoxide at atmospheric pressure or at an increased pressure, in the presence of a suitable palladium-catalyst (e.g. palladium on charcoal), an appropriate base such as triethylamine and a suitable solvent such as dioxane.

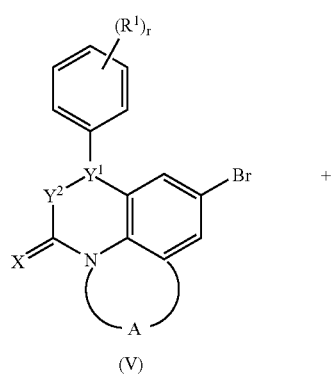

(V)

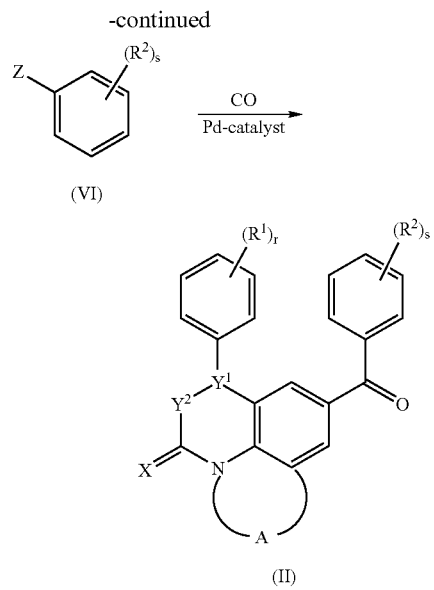

a) Intermediate ketons of formula (II) can also be prepared by reacting intermediate compounds of formula (VII) with intermediate compounds of formula (VIII) in the presence of a suitable solvent such as tetrahydrofuran.

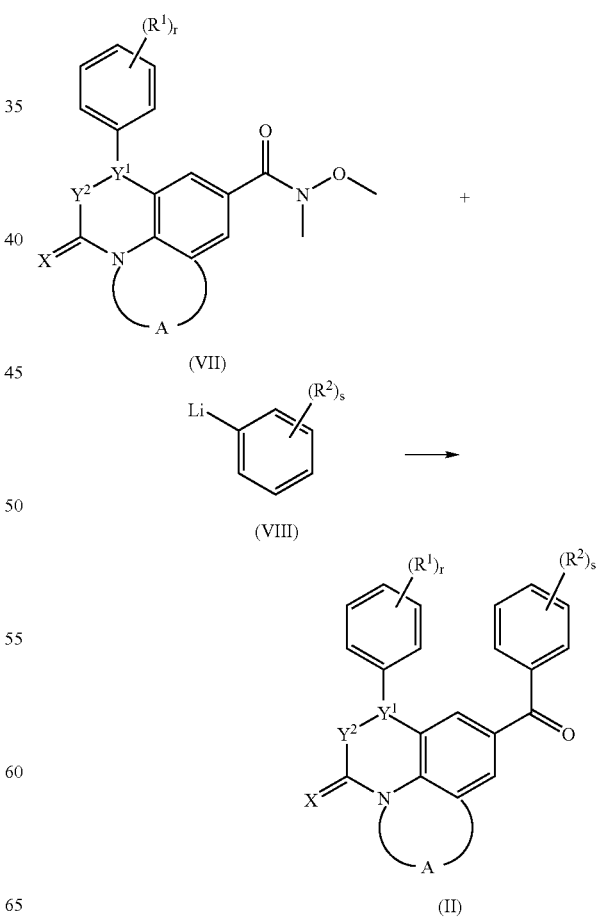

b) The intermediate compounds of formula (VII) can be prepared by reacting intermediate compounds of formula (V) with intermediate compounds of formula (IX) and addition of carbon monoxide at atmospheric pressure or at an increased pressure, in the presence of a suitable palladium-catalyst (e.g. palladium on charcoal), an appropriate base such as triethylamine and a suitable solvent such as dioxane.

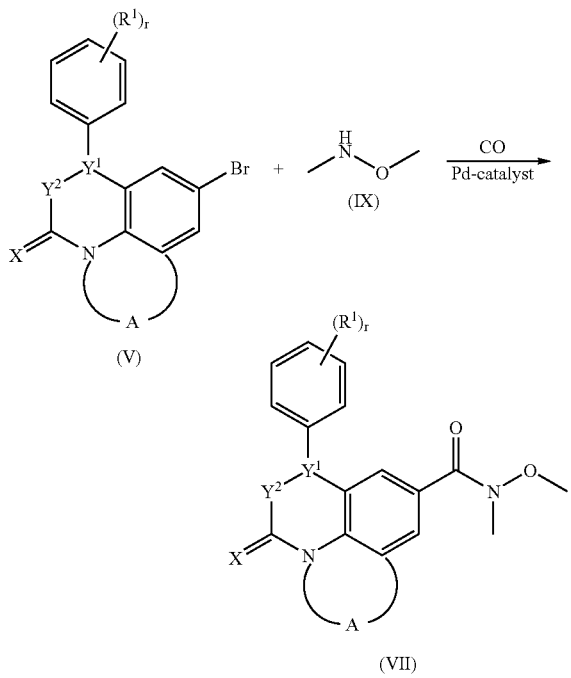

c) The intermediate compounds of formula (V-a) wherein >Y¹—Y²— is a trivalent radical of formula (y-2) wherein R⁵ is hydrogen can be converted in intermediate compounds of formula (V-b) wherein >Y¹—Y²²— is a trivalent radical of formula (y-1) wherein R⁵ is hydrogen, in the presence of iodium, potassium acetate and a suitable solvent such as acetic acid.

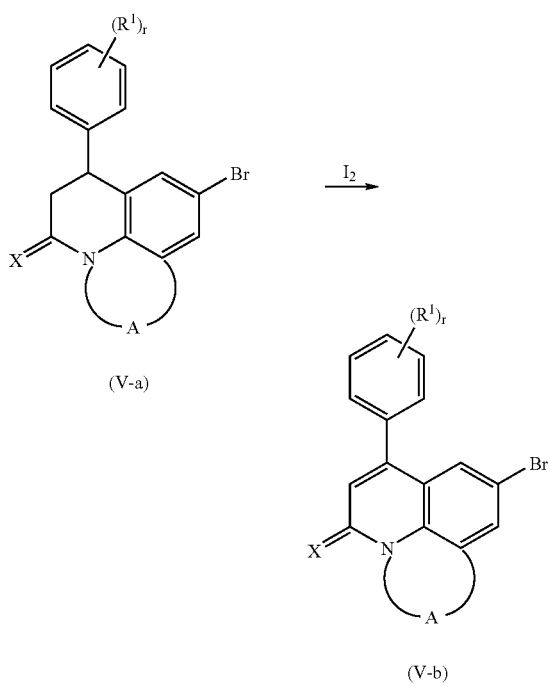

d) Intermediate compounds of formula (V-a) wherein X is oxygen, can be prepared by reacting intermediate compounds of formula (XI) with polyphosphoric acid (PPA).

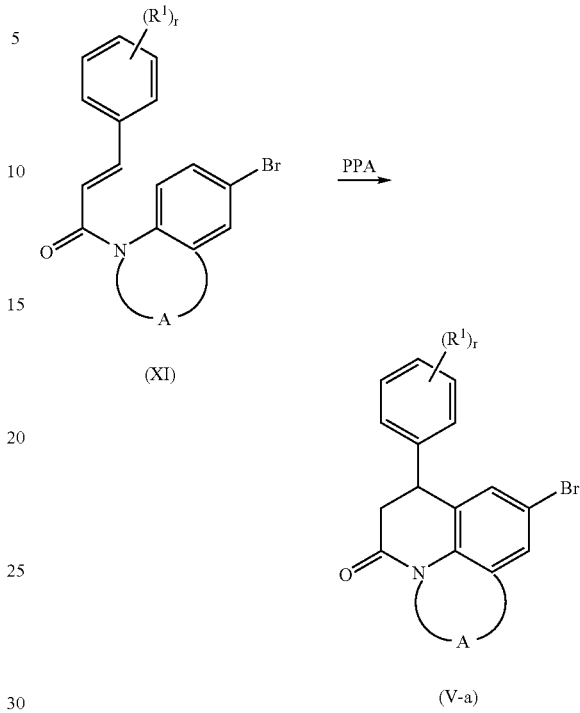

e) Intermediate compounds of formula (XI) can be prepared by reacting intermediate compounds of formula (XII) with intermediate compounds of formula (XIII) in the presence of an appropriate base such as triethylamine and a suitable solvent such as dichloromethane (DCM).

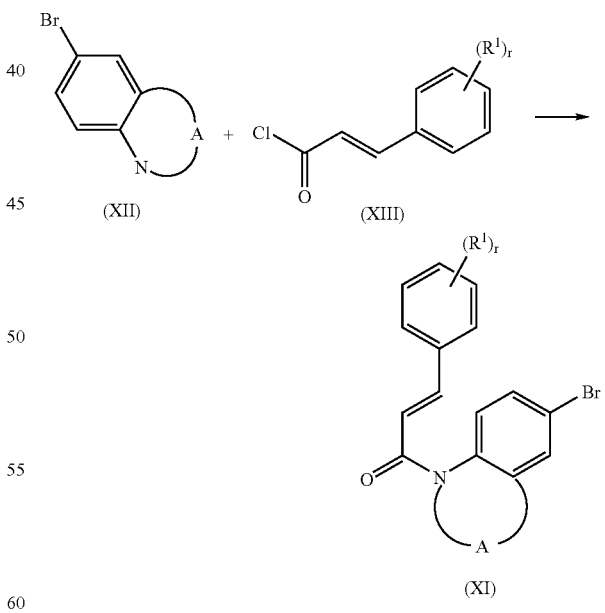

The compounds of formula (I) and some of the intermediates have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575-4580, 1995). Hence, pharmacologically targeting mutant ras oncogenes could conceivably suppress solid tumor growth in vivo, in part, by inhibiting tumor-induced angiogenesis.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours expressing an activated ras oncogene by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumours in which ras is activated due to mutation or overexpression of tyrosine kinase oncogenes, may be inhibited by the compounds of this invention.

The compound according to the invention can be used for other therapeutic purposes, for example:

a) the sensitisation of tumours to radiotherapy by administering the compound according to the invention before, during or after irradiation of the tumour for treating cancer, for example as described in WO 00/01411;

b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;

c) inhibiting smooth muscle cell proliferation including vascular proliferative disorders, atherosclerosis and restenosis, for example as described in WO 98/55124;

d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosus, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;

j) suppressing induction of inducible nitric oxide including nitric oxide or cytokine mediated disorders, septic shock, inhibiting apoptosis and inhibiting nitric oxide cytotoxicity;

k) treating malaria.

The compounds of present invention may be particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anticancer agents for example selected from platinum coordination compounds for example cisplatin or carboplatin, taxane compounds for example paclitaxel or docetaxel, camptothecin compounds for example irinotecan or topotecan, anti-tumour vinca alkaloids for example vinblastine, vincristine or vinorelbine, anti-tumour nucleoside derivatives for example 5-fluorouracil, gemcitabine or capecitabine, nitrogen mustard or nitrosourea alkylating agents for example cyclophosphamide, chlorambucil, carmustine or lomustine, anti-tumour anthracycline derivatives for example daunorubicin, doxorubicin or idarubicin; HER2 antibodies for example trastzumab; and anti-tumour podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can be administered to a patient as described above, in conjunction with irradiation. Such treatment may be especially beneficial, as farnesyl transferase inhibitors can act as radiosensitisers, for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumour by radionuclides can be external or internal.

Preferably, the administration of the farnesyl transferase inhibitor commences up to one month, in particular up to 10 days or a week, before the irradiation of the tumour. Additionally, it is advantageous to fractionate the irradiation of the tumour and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumour, its location, the patient's reaction to chemo- or radiotherapy and ultimately is for the physician and radiologists to determine in each individual case.

The present invention also concerns a method of cancer therapy for a host harboring a tumour comprising the steps of
- administering a radiation-sensitizing effective amount of a farnesyl protein transferase inhibitor according to the invention before, during or after
- administering radiation to said host in the proximity to the tumour.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.001 mg/kg to 100 mg/kg body weight, and in particular from 0.1 mg/kg to 100 mg/kg body weight. It may be appropriate to administer the required dose as two, three, four or more sub-doses at appropriate intervals throughout the day. Said sub-doses may be formulated as unit dosage forms, for example, containing 0.1 to 500 mg, and in particular 10 mg to 500 mg of active ingredient per unit dosage form.

The following examples are provided for purposes of illustration.

Hereinafter "THF" means tetrahydrofuran, "DME" means 1,2-dimethoxyethane, "EtOAc" means ethyl acetate, "eq" means equivalent, "DCM" means dichloromethane, "DMF" means dimethylformamide and "BuLi" means n-butyl lithium.

A. Preparation of the Intermediates

EXAMPLE A1 a) A mixture of (±)-6-(3-chlorophenyl)-1,2,5,6-tetrahydro-4H-pyrrolo[3,2,1-ij]quinolin-4-one (described in International Application WO98/40383) (0.211 mol) in polyphosporic acid (600 g) was stirred at 140° C. overnight. 4-Iodobenzoic acid (0.422 mol) was added portionwise. The mixture was stirred at 140° C. overnight then brought to 100° C. and poured out into ice water. DCM was added. The precipitate was filtered over celite and washed with DCM. The filtrate was extracted with DCM. The organic layer was basified with $K_2CO_3$ (10%) then washed with water, dried ($MgSO_4$), filtered, and the solvent was evaporated. The residue was purified by column chromatography over silica gel (15-35 μm) (eluent: $CH_2Cl_2$/EtOAc; 95/5). The pure fractions were collected and the solvent was evaporated, yielding 35 g (32%). A part of this fraction (1 g) was crystallized from $CH_3CN$/2-propanone (warm). The precipitate was filtered off and dried under a vacuo, yielding 0.77 g of 6-(3-chlorophenyl)-1,2,5,6-tetrahydro-8-(4-iodobenzoyl)-4H-pyrrolo[3,2,1-ij]quinolin-4-one, melting point 275° C. (intermediate 1).

b) Acetic acid, potassium salt (0.22 mol) then iodine (0.147 mol) were added at room temperature to a solution of (intermediate 1) (0.061 mol) in acetic acid (300 ml). The mixture was stirred at 130° C. for 72 hours, poured out into $Na_2S_2O_3$ 1 M/ice and extracted with DCM. The organic layer was washed with $K_2CO_3$ 10%, separated, dried ($MgSO_4$), filtered, and the solvent was evaporated. The residue was purified by column chromatography over silica gel (20-40 μm)(eluent: $CH_2Cl_2$/$CH_3OH$;95/5 to 60/40). Two fractions were collected and the solvent was evaporated. Yielding: 4.0 g of starting material and 26.5 g F1 (84%). A part (0.7 g) of F1 was crystallized from 2-propanone. The precipitate was filtered off and dried, yielding 0.61 g of 6-(3-chlorophenyl)-1,2-dihydro-8-(4-iodobenzoyl)-4H-pyrrolo[3,2,1-ij]quinolin-4-one, melting point 202° C. (intermediate 2).

c) A mixture of (intermediate 2) (0.0219 mol) and tosylmethyl isocyanide (0.0284 mol) was added at −5° C. to DME (330 ml) under $N_2$ flow. Ethanol (33 ml) then 2-methyl,2-propanol potassium salt (0.0525 mol) was added portionwise at 5° C. The mixture was stirred at 10° C. for 1 hour and 30 minutes, poured out into ice water and extracted with EtOAc. The organic layer was separated, dried ($MgSO_4$), filtered, and the solvent was evaporated. The residue was purified by column chromatography over silica gel (15-35 μm) (eluent: toluene/EtOAc; 50/50). The pure fractions were collected and the solvent was evaporated, yielding: 1.9 g of 6-(3-chlorophenyl)-1,2-dihydro-α-(4-iodophenyl)-4-oxo-4H-pyrrolo[3,2,1-ij]quinoline-8-acetonitrile (intermediate 3).

d) A mixture of (intermediate 3) (0.0195 mol) in acetic acid (30 ml), sulfuric acid (30 ml) and water (30 ml) was stirred and refluxed overnight and poured out into ice water. The precipitate was filtered, washed with diethyl ether and dried under a vaccuo, yielding (quantitative) 6-(3-chlorophenyl)-1,2-dihydro-α-(4-iodophenyl)-4-oxo-4H-pyrrolo[3,2,1-ij]quinoline-8-acetic acid (intermediate 4).

e) N'-(ethylcarbonimidoyl)-N,N-dimethyl-1,3-propanediamine, monohydrochloride (0.021 mol), 1-hydroxybenzotriazole (0.021 mol) then N-methyl-hydrazinecarbothioamide (0.021 mol) were added to a mixture of (intermediate 4) (0.017 mol) in THF (95 ml). The mixture was stirred at room temperature for 48 hours and poured out into ice water. The precipitate was filtered off and dried, yielding 8.9 g (83%) of 6-(3-chlorophenyl)-1,2-dihydro-α-(4-iodophenyl)-4-oxo-, 2-[(methylamino)carbonothioyl]hydrazide 4H-pyrrolo[3,2,1-ij]quinoline-8-acetic acid (intermediate 5). The product was used without further purification in the next reaction step.

f) $CH_3ONa$ (30%) in methanol (0.0133 mol) was added to a mixture of (intermediate 5) (0.0133 mol) in methanol (110 ml). The mixture was stirred and refluxed for 3 hours then cooled, poured out into ice water and extracted with DCM. The organic layer was separated, dried ($MgSO_4$), filtered, and the solvent was evaporated. The residue was purified by column chromatography over silica gel (15-40 μm) (eluent: $CH_2Cl_2$/$CH_3OH$/$NH_4OH$; 95/5/0.1). The pure fractions were collected and the solvent was evaporated, yielding 4.35 g (53.5%) of 6-(3-chlorophenyl)-1,2-dihydro-8-[(4-iodophenyl)(5-mercapto-4-methyl-4H-1,2,4-triazol-3-yl)methyl]-4H-pyrrolo[3,2,1-ij]quinolin-4-one (intermediate 6).

EXAMPLE A2 n-BuLi (0.0166 mol) was added slowly at −78° C. to a solution of 2,4-dihydro-4-methyl-3H-1,2,4-triazole-3-thione (0.0082 mol) in THF (50 ml) under $N_2$ flow. The mixture was stirred at 0° C. for 1 hour, then cooled to −78° C. 9-(4-chlorobenzoyl)-7-(3-chlorophenyl)-2,3-dihydro-1H,5H-benzo[ij]quinolizin-5-one (described in International Application WO98/40383) (0.0046 mol) was added portionwise. The mixture was stirred at room temperature for 4 hours, poured out on ice and extracted with EtOAc. The organic layer was separated, dried ($MgSO_4$), filtered, and the solvent was evaporated. The residue (2.32 g) was purified by column chromatography over silica gel (15-40 μm) (eluent: $CH_2Cl_2$/$CH_3OH$/$NH_4OH$ 98/2/0.1 to 96/4/0.1). The pure fractions were collected and the solvent was evaporated. The residue (1 g, 40%). was crystallized from acetonitril. The precipitate was filtered off and dried, yielding 0.52 g (21%) of 7-(3-chlorophenyl)-9-[(4-chlorophenyl)hydroxy(5-mercapto-4-methyl-4H-1,2,4-triazol-3-yl)methyl]-2,3-dihydro-1H,5H-benzo[ij]quinolizin-5-one hydrate (1:1), melting point 160° C. (intermediate 7).

EXAMPLE A3 a) Triethylamine (0.05 mol) was added to a mixture of 5-bromo-2,3-dihydro-1H-indole (0.025 mol) in DCM (35 ml). A solution of 3-(3-chlorophenyl)-2-propenoyl chloride (0.0365 mol) in DCM (20 ml) was added dropwise. The mixture was stirred at room temperature overnight. Water was added. The mixture was extracted with DCM. The organic layer was separated, dried ($MgSO_4$), filtered, and the solvent was evaporated. The residue (11.34 g) was dissolved in DCM and crystallized from diethyl ether. The precipitate was filtered off and dried to give 3.17 g of intermediate 8. The filtrate was evaporated. The residue was dissolved in DCM and crystallized from diethyl ether. The precipitate was filtered off and dried, yielding 2.17 g (59%) of 5-bromo-1-[(2E)-3-(3-chlorophenyl)-1-oxo-2-propenyl]-2,3-dihydro-1H-indole (intermediate 8).

b) A mixture of intermediate 8 (0.012 mol) and polyphosporic acid (60 g) was stirred at 140° C. overnight, poured out into ice water and $NH_4OH$ and extracted with DCM. The organic layer was separated, dried ($MgSO_4$), filtered, and the solvent was evaporated. The residue (5.09 g) was purified by column chromatography over silica gel (20-45 μm) (eluent: cyclohexane/EtOAc 60/40). The pure fractions were collected and the solvent was evaporated, yielding 1.7 g of 8-bromo-6-(3-chlorophenyl)-1,2,5,6-tetrahydro-4H-pyrrolo[3,2,1-ij]quinolin-4-one (intermediate 9).

c) $I_2$ (0.0112 mol) and potassium acetate (0.0169 mol) were added to a solution of intermediate 9 (0.0047 mol) in acetic acid (12 ml). The mixture was stirred at 140° C. for 2 days. After the first night, $I_2$ (0.584 g, 0.5 eq) and potassium acetate (0.345 g, 0.75 eq) were added. The mixture was poured out into ice water and $NaHSO_3$. The precipitate was filtered. DCM was added to the filtrate. The mixture was extracted with DCM. The organic layer was washed with $H_2O$/$NH_4OH$, dried ($MgSO_4$), filtered and the solvent was evaporated. The residue (2.4 g) was purified by column chromatography over silica gel (35-70 μm)(eluent: $CH_2Cl_2$/$CH_3OH$ 98/2). The pure fractions were collected and the solvent was evaporated, yielding 1.38 g (82%) of 8-bromo-6-(3-chlorophenyl)-1,2-dihydro-4H-pyrrolo[3,2,1-ij]quinolin-4-one (intermediate 10).

d) A mixture of intermediate 10 (0.0025 mol), N-methoxymethanamine, hydrochloride (0.0055 mol), Pd(PPh$_3$)$_4$ (0.00025 mol) and triethylamine (0.0124 mol) in dioxane (30 ml) was stirred at 100° C. for 3 days under a 5 bar pressure of CO and poured out into ice water. DCM was added. The mixture was filtered over celite and extracted with DCM. The organic layer was separated, dried (MgSO$_4$), filtered, and the solvent was evaporated. The residue (1.71 g) was purified by column chromatography over silica gel (15-40 μm) (eluent: CH$_2$Cl$_2$/CH$_3$OH/ NH$_4$OH 97/3/0.1). The pure fractions were collected and the solvent was evaporated. The residue (0.56 g) was crystallized from DCM/diethyl ether. The precipitate was filtered off and dried, yielding 0.159 g of 6-(3-chlorophenyl)-1,2-dihydro-N-methoxy-N-methyl-4-oxo-4H-pyrrolo[3,2,1-ij]quinoline-8-carboxamide, melting point 162° C. (intermediate 11).

e) Phenyl-lithium (0.00065 mol) was added at −78° C. to a solution of intermediate 11 (0.00054 mol) in THF (4 ml) under N$_2$ flow. The mixture was stirred at −78° C. for 2 hours. Water and ice were added. The mixture was extracted with EtOAc. The organic layer was separated, dried (MgSO$_4$), filtered, and the solvent was evaporated. The residue (0.172 g) was purified by column chromatography over silica gel (10 μm) (eluent: DCM 100). The pure fractions were collected and the solvent was evaporated, yielding 0.011 g (5%) of 8-benzoyl-6-(3-chlorophenyl)-1,2-dihydro-4H-pyrrolo[3,2,1-ij]quinolin-4-one (intermediate 12).

EXAMPLE A4

An Alternative Way for the Preparation of Intermediate 12 Starting from Intermediate 10

A mixture of intermediate 10 (0.00078 mol), phenyl-boronic acid (0.0011 mol), Pd(PPh$_3$)$_4$ (0.078 mol) and triethylamine (0.0038 mol) in dioxane (30 ml) was stirred at 100° C. for 4 days under a 5 bar pressure of CO and poured out into ice water. DCM was added. The mixture was filtered over celite. Celite was washed with DCM. The organic layer was separated, dried (MgSO$_4$), filtered, and the solvent was evaporated.

The residue (0.31 g) was purified by column chromatography over silica gel (10 μm) (eluent: DCM100). The pure fractions were collected and the solvent was evaporated, yielding 0.075 g (25%) of 8-benzoyl-6-(3-chlorophenyl)-1,2-dihydro-4H-pyrrolo[3,2,1-ij]quinolin-4-one (intermediate 12).

EXAMPLE A5 nBuLi 1.6M in hexane (0.0086 mol) was added at −78° C. to a solution of 2,4-dihydro-4-methyl-3H-1,2,4-triazole-3-thione (0.0043 mol) in THF (25 ml) under N$_2$ flow. The mixture was stirred at 0° C. for 1 hour, then cooled to −78° C. 8-(4-chlorobenzoyl)-6-(3-chlorophenyl)-2H,4H-oxazolo[5,4,3-ij]quinolin-4-one (0.0024 mol) described in International Publication WO98/40383, was added portionwise. The mixture was stirred at room temperature for 4 hours, poured out into ice water and extracted with EtOAc. The organic layer was separated, dried (MgSO$_4$), filtered, and the solvent was evaporated. The residue (1.38 g) was purified by column chromatography over silica gel (15-40 μm) (eluent: CH$_2$Cl$_2$/ CH$_3$OH/NH$_4$OH97/3/0.1). The pure fractions were collected and the solvent was evaporated. A part of the residue (0.049 g) was purified by column chromatography over silica gel (10 μm) (eluent: CH$_2$Cl$_2$/CH$_3$OH 98/2). The pure fractions were collected and the solvent was evaporated, yielding 0.018 g (1%) of 6-(3-chlorophenyl)-8-[(4-chlorophenyl)hydroxy(5-mercapto-4-methyl-4H-1,2,4-triazol-3-yl)methyl]-2H,4H-oxazolo[5,4,3-ij]quinolin-4-one, melting point: 193° C. (intermediate 13).

B. Preparation of the Final Compounds

EXAMPLE B1

Sodium nitrite (0.0057 mol) was added at 10° C. to a mixture of nitric acid (10.5 ml) and water (10.5 ml). A mixture of (intermediate 6) (0.0057 mol) in THF (35 ml) was added dropwise. The mixture was stirred at 10° C. for 1 hour, poured out into ice water, basified with K$_2$CO$_3$ solid and extracted with EtOAc. The organic layer was separated, dried (MgSO$_4$), filtered, and the solvent was evaporated. The residue was purified by column chromatography over silica gel (15-40 μm) (eluent: CH$_2$Cl$_2$/CH$_3$OH/NH$_4$OH; 94/6/0.1). The pure fractions were collected and the solvent was evaporated, yielding 1.35 g (37.7%). A part of this fraction (0.55 g) was crystallized from CH$_3$CN/diethyl ether. The precipitate was filtered off and dried, yielding 0.35 g (10.5%) of 6-(3-chlorophenyl)-1,2-dihydro-8-[(4-iodophenyl)(4-methyl-4H-1,2,4-triazol-3-yl)methyl]-4H-pyrrolo[3,2,1-ij]quinolin-4-one. hydrate (1:1), melting point 194° C. (compound I). Intermediate 13 can be converted in a similar way into a similar endproduct.

EXAMPLE B2

N$_2$ was bubbled in a solution of 6-(3-chlorophenyl)-1,2-dihydro-8-[(4-iodophenyl)(4-methyl-4H-1,2,4-triazol-3-yl)methyl]-4H-pyrrolo[3,2,1-ij]quinolin-4-one, obtained in example B1 (0.002 mol) in DMF (20 ml) for 1 hour. Zn(CN)$_2$ (0.0031 mol) then Pd(PPh$_3$)$_4$ (0.002 mol) were added. The mixture was stirred at 80° C. for 4 hours, cooled, poured out into ice water, filtered over celite and extracted with DCM. The organic layer was separated, dried (MgSO$_4$), filtered, and the solvent was evaporated. The residue was purified by column chromatography over silica gel (15-35 μm)(eluent: CH$_2$Cl$_2$/CH$_3$OH/NH$_4$OH 95/5/0.1 to 94/6/0.2). The pure fractions were collected and the solvent was evaporated, yielding 0.41 g (41%) of 4-[[6-(3-chlorophenyl)-1,2-dihydro-4-oxo-4H-pyrrolo[3,2,1-ij]quinolin-8-yl](4-methyl-4H-1,2,4-triazol-3-yl)methyl]- benzonitrile, melting point 174° C. (compound 2).

EXAMPLE B3

Nitric acid (2 ml) was added at 0° C. to a solution of sodium nitrite (0.0014 mol) in water (2 ml). The mixture was stirred for 5 minutes. A solution of (intermediate 7) (0.0012 mol) in THF (8 ml) was added dropwise. The mixture was stirred at 0° C. for 1 hour, poured out into K$_2$CO$_3$ 10% and extracted with EtOAc. The organic layer was separated, dried (MgSO$_4$), filtered, and the solvent was evaporated. The residue (1.1 g) was purified by column chromatography over silica gel (15-40 μm) (eluent: CH$_2$Cl$_2$/CH$_3$OH/NH$_4$OH 94/6/0.2). The pure fractions were collected and the solvent was evaporated. The residue (0.52 g) was crystallized from acetonitrile. The precipitate was filtered off and dried; yielding 0.22 g (33%) of 7-(3-chlorophenyl)-9-[(4-chlorophenyl)hydroxy(4-methyl-4H-1,2,4-triazol-3-yl)methyl]-2,3-dihydro-1H,5H-benzo[ij] quinolizin-5-one, melting point 183° C. (compound 3).

EXAMPLE B4

Sulfuric acid concentrated (2 drops) was added to a solution of compound 4 6-(3-chlorophenyl)-8-[(4-fluorophenyl)hydroxy(4-methyl-4H-1,2,4-triazol-3-yl)methyl]-1,2-dihydro-4H-pyrrolo[3,2,1-ij]quinolin-4-one (which was made in a similar way as described in example B1) (0.0001 mol) in acetonitrile (1 ml). The mixture was stirred and refluxed overnight. Water and $NH_4OH$ were added. The mixture was extracted with DCM. The organic layer was separated, dried ($MgSO_4$), filtered, and the solvent was evaporated. The residue (0.056 g) was taken up in DCM. The precipitate was filtered, washed with diethyl ether and dried; yielding 0.054 g (100%) of N-[[6-(3-chlorophenyl)-1,2-dihydro-4-oxo-4H-pyrrolo[3,2,1-ij]quinolin-8-yl](4-fluorophenyl)(4-methyl-4H-1,2,4-triazol-3-yl)methyl]-acetamide, melting point 196° C. (compound 5).

EXAMPLE B5

Sulfuric acid concentrated (0.3 ml) was added to a mixture of compound 3 (0.0005 mol) in methanol (6 ml). The mixture was stirred and refluxed for 72 hours, poured out into ice water, basified with $NH_4OH$ and extracted with DCM. The organic layer was separated, dried ($MgSO_4$), filtered, and the solvent was evaporated. The residue (0.268 g) was purified by column chromatography over silica gel (10 μm) (eluent: $CH_2Cl_2/CH_3OH$ 98/2). The pure fractions were collected and the solvent was evaporated, yielding 0.05 g (17%) of 7-(3-chlorophenyl)-9-[(4-chlorophenyl)methoxy(4-methyl-4H-1,2,4-triazol-3-yl)methyl]-2,3-dihydro-1H,5H-benzo[ij]quinolizin-5-one, melting point 132° C. (compound 6).

EXAMPLE B6

Sulfuric acid concentrated (2 drops) was added to a mixture of compound 4 (which was made in a similar way as described in example B1) (0.0002 mol) in 1,2-ethanediol (1 ml). The mixture was stirred at 125° C. overnight. Water and ice were added. $NH_4OH$ (1 drop) was added. The precipitate was filtered, washed with diethyl ether and dried. The residue (0.118 g) was purified by column chromatography over silica gel (10 μm)(eluent: toluene/iPrOH/$NH_4OH$ 70/29/1). The pure fractions were collected and the solvent was evaporated, yielding 0.058 g (53%) of 6-(3-chlorophenyl)-8-[(4-fluorophenyl)(2-hydroxyethoxy)(4-methyl-4H-1,2,4-triazol-3-yl)methyl]-1,2-dihydro-4H-pyrrolo[3,2,1-ij]quinolin-4-one, melting point 138° C. (compound 7).

EXAMPLE B7

A mixture of compound 4 (which was made in a similar way as described in example B1) (0.0002 mol) in 1,3-dimethyl-2-imidazolidinone (0.6 ml) was stirred at room temperature for 10 minutes. Thionyl chloride (0.0008 mol) was added dropwise at room temperature. The mixture was stirred at room temperature for 3 hours and 30 minutes. 4H-imidazole (0.004 mol) was added portionwise. The mixture was stirred at room temperature overnight, poured out into ice water. The precipitate was filtered off and dried, yielding 0.033 g of 6-(3-chlorophenyl)-8-[(4-fluorophenyl)-1H-imidazol-1-yl(4-methyl-4H-1,2,4-triazol-3-yl)methyl]-1,2-dihydro-4H-pyrrolo[3,2,1-ij]quinolin-4-one (compound 8).

EXAMPLE B8

A mixture of compound 4 (which was made in a similar way as described in example B1) (0.0002 mol) in 1,3-dimethyl-2-imidazolidinone (0.6 ml) was stirred for 10 minutes. Thionyl chloride (0.0008 mol) was added dropwise at room temperature. The mixture was stirred at room temperature for 3 hours and 30 minutes then added dropwise at 5° C. to $NH_3/CH_3OH$ 7N (0.004 mol). The mixture was stirred at room temperature overnight, poured out into ice water and extracted with DCM. The organic layer was separated, dried ($MgSO_4$), filtered, and the solvent was evaporated. Water was added. The mixture was stirred at room temperature for 1 hour. The precipitate was filtered, washed with diethyl ether and dried. The residue (0.048 g) was taken up in diethyl ether. The precipitate was filtered off and dried. Diethyl ether was added. The mixture was evaporated, yielding 0.034 g of 8-[amino(4-fluorophenyl)(4-methyl-4H-1,2,4-triazol-3-yl)methyl]-6-(3-chlorophenyl)-1,2-dihydro-4H-pyrrolo[3,2,1-ij]quinolin-4-one (compound 9).

EXAMPLE B9

Benzyltriethylammonium chloride (0.0003 mol) then iodomethane (0.0006 mol) was added to a solution of compound 4 (which was made in a similar way as described in example B1) (0.0004 mol) in THF (2 ml) and NaOH 3N (2 ml). The mixture was stirred at room temperature for 3 days. Water was added. The mixture was extracted with EtOAc. The organic layer was separated, dried ($MgSO_4$), filtered, and the solvent was evaporated. The residue (0.217 g) was purified by column chromatography over silica gel (eluent: DCM/evaporated. 10 μm). The pure fractions were collected and the solvent was evaporated. The residue (0.08 g) was crystallized from 2-propanone/DIPE. The precipitate was filtered off and dried. The filtrate was evaporated, yielding 0.04 g (20%) of 6-(3-chlorophenyl)-8-[(4-fluorophenyl)methoxy(4-methyl-4H-1,2,4-triazol-3-yl)methyl]-1,2-dihydro-4H-pyrrolo[3,2,1-ij]quinolin-4-one (compound 10).

Table F-1 and F-2 lists the compounds that were prepared according to one of the above Examples. The following abbreviations were used in the tables: Co. No. stands for Compound Number, Ex. [Xn°] referred to the same method as described in the Xn° example.

TABLE F-1 intermediates

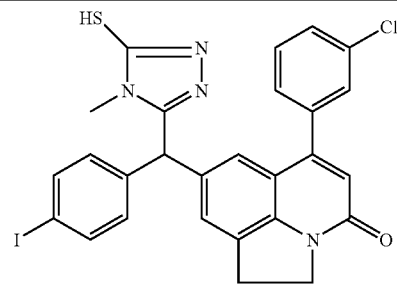

Intermediate 6.; Ex. [A1]

TABLE F-1-continued
intermediates
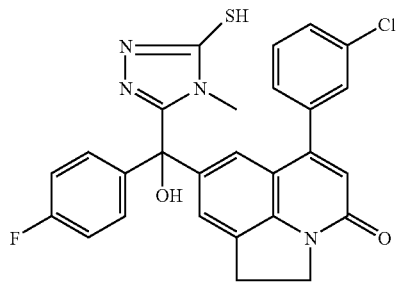
Intermediate 14; Ex. [A1]; mp. 228° C.
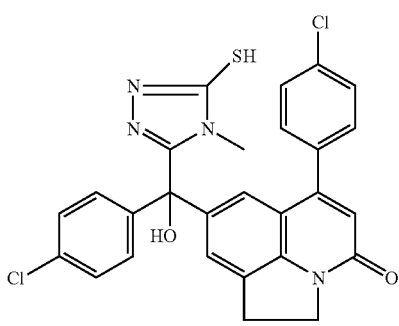
Intermediate 15; Ex. [A1]; mp. 154° C.
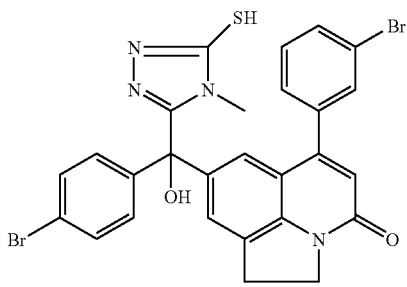
Intermediate 16; Ex. [A1]; mp. 210° C.
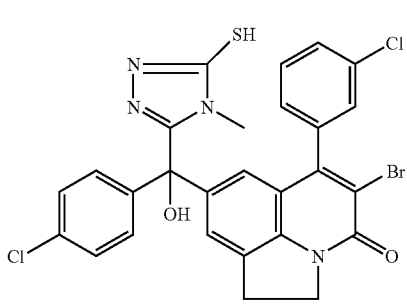
Intermediate 17; Ex. [A1]
TABLE F-1-continued
intermediates
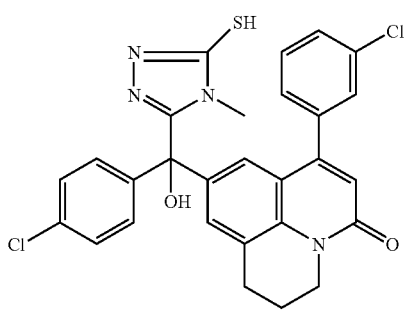
. H2O (1:1); Intermediate 7 ; Ex. [A2]; mp. 160° C.
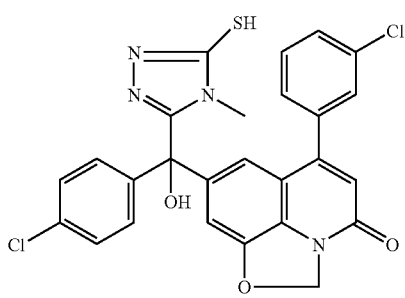
Intermediate 13 ; Ex. [A5]; mp. 193° C.
Table F2
Final Compounds
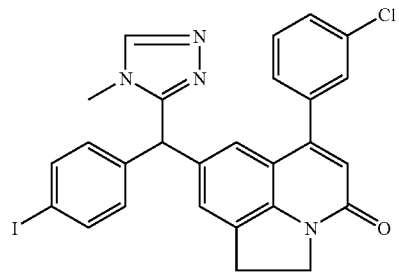
H$_2$O (1:1);Co. No. 1; Ex. [B1]; mp. 194° C.

Table F2-continued
Final Compounds
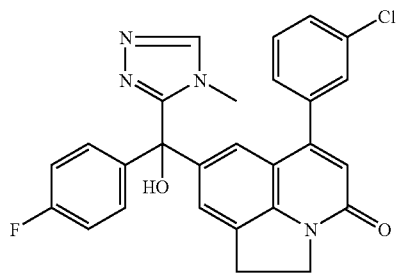
Co. No. 4; Ex. [B1]; mp. 188° C.
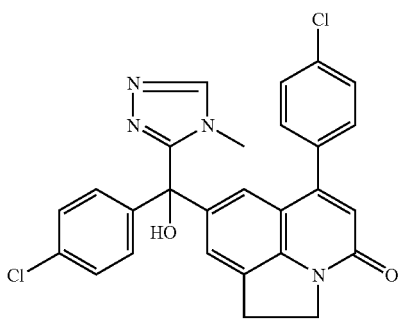
Co. No. 11; Ex. [B1];
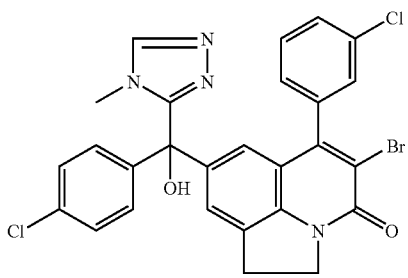
Co. No. 12; Ex. [B1]; mp. 200° C.
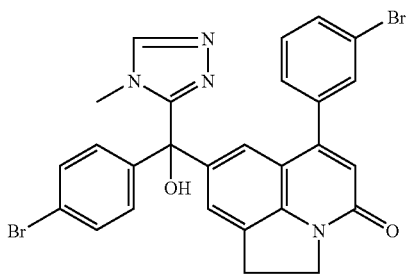
Co. No. 13; Ex. [B1]; mp. 181° C.
Table F2-continued
Final Compounds
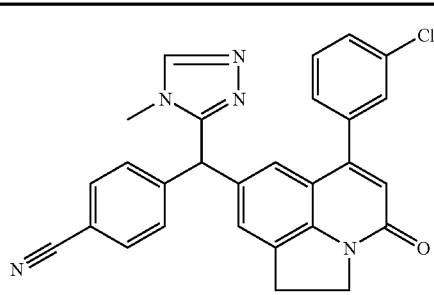
Co. No. 2; Ex. [B2]; mp. 174° C.
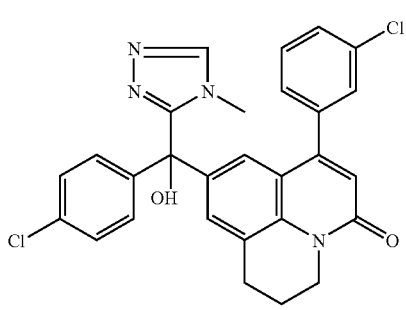
Co. No. 3; Ex. [B3]; mp. 183° C.
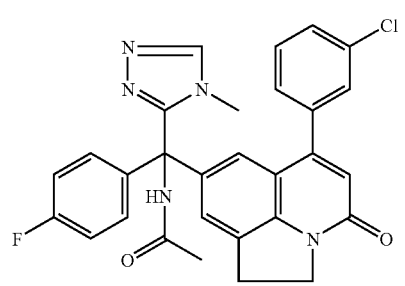
Co. No. 5; Ex. [B4]; mp. 196° C.
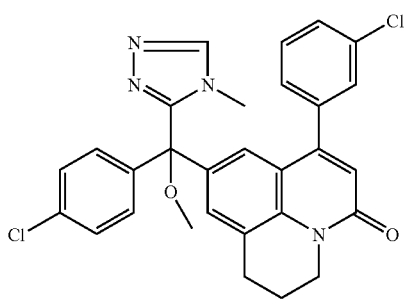
Co. No. 6; Ex. [B5]; mp. 132° C.

Table F2-continued

Final Compounds

Co. No. 7; Ex. [B6]; mp. 138° C.

Co. No. 8; Ex. [B7]

Co. No. 9; Ex. [B8]

Co. No. 10; Ex. [B9]

C. PHARMACOLOGICAL EXAMPLE

EXAMPLE C.1

"In Vitro Asay for Inhibition of Farnesyl Protein Transferase"

An in vitro assay for inhibition of farnesyl transferase was performed essentially as described in WO 98/40383, pages 33-34. When appropriate, $IC_{50}$-values (concentration of the drug, needed to reduce the product of the enzymatic reaction, to 50% of the conrol) were computed using probit analysis for graded data (Finney, D. J., Probit Analuses, $2^{nd}$ Ed. Chapter 10, Graded Responses, Cambridge Univerity Press, Cambridge 1962). Herein (see table F-3) the effects of test compounds are expressed as $pIC_{50}$ (the negative log value of the $IC_{50}$-value). Also the intermediate compounds described in the table F-1 show activity in the in vitro assay for inhibition of farnesyl protein transferase.

EXAMPLE C.2

"Ras-Transformed Cell Phenotype Reversion Assay"

The ras-transformed cell phenotype reversion assay was performed essentially as described in WO 98/40383, pages 34-36.

EXAMPLE C.3

"Farnesyl Protein Transferase Inhibitor Secondary Tumour Model"

The farnesyl protein transferase inhibitor secondary tumour model was used as described in WO 98/40383, page 37.

TABLE F-3

| Co. No. | Enzyme activity pIC50 |
| --- | --- |
| 1 | 7.669 |
| 2 | 8.695 |
| 3 | 8.087 |
| 4 | 8.239 |
| 11 | >7 |
| 12 | <7 |
| 13 | 8.232 |
| 5 | 8.469 |
| 6 | >7 |
| 7 | 8.403 |
| 8 | 8.416 |
| 9 | 8.526 |
| 10 | 7.533 |

D. COMPOSITION EXAMPLE

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

We claim:

1. A compound of formula (I):

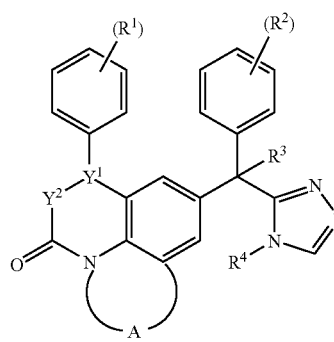

(I)

or a pharmaceutically acceptable salt or N-oxide or stereochemically isomeric form thereof, wherein
   -A- is a bivalent radical of formula selected from the group consisting of

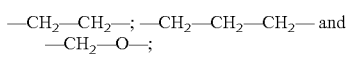

$>Y^1-Y^2-$ is $>C=CR^5-$ wherein $R^5$ is hydrogen or halo
   $R^1$ is selected from the group consisting of hydrogen or halo;
   $R^2$ is selected from the group consisting of hydrogen, halo, or cyano;
   $R^3$ is selected from the group consisting of hydrogen, N-imidazolyl, —O—$R^6$, and —NHR$^8$;
   wherein
   $R^6$ is selected from the group consisting of hydrogen, $C_{1-6}$alkyl and hydroxy$C_{1-6}$alkyl;
   $R^8$ is selected from the group consisting of hydrogen and $C_{1-6}$alkylcarbonyl; and
   $R^4$ is hydrogen or $C_{1-6}$alkyl.

2. A compound according to claim 1 in which $R^2$ is halo or cyano;
   $R^3$ is selected from the group consisting of hydrogen, hydroxy, amino, $C_{1-6}$alkyloxy, hydroxy$C_{1-6}$alkyloxy, $C_{1-6}$alkylcarbonylamino and N-imidazolyl;
   and $R^4$ is $C_{1-2}$alkyl.

3. A compound according to claim 1 selected from the group consisting of:
   6-(3-chlorophenyl)-1,2-dihydro-8-[(4-iodophenyl)(4-methyl-4H-1,2,4-triazol-3-yl) methyl]-4H-pyrrolo[3,2,1-ij]quinolin-4-one;
   4-[[6-(3-chlorophenyl)-1,2-dihydro-4-oxo-4H-pyrrolo[3,2,1-ij]quinolin-8-yl](4-methyl -4H-1,2,4-triazol-3-yl) methyl]- benzonitrile;
   7-(3-chlorophenyl)-9-[(4-chlorophenyl)hydroxy(4-methyl-4H-1,2,4-triazol-3-yl) methyl]-2,3-dihydro-1H, 5H-benzo[iJ]quinolizin-5-one;
   6-(3-chlorophenyl)-8-[(4-fluorophenyl)hydroxy(4-methyl-4H-1,2,4-triazol-3-yl) methyl]-1,2-dihydro-4H-pyrrolo[3,2,1-ij]quinolin-4-one;
   6-(4-chlorophenyl)-8-[(4-chlorophenyl)hydroxy(4-methyl-4H-1,2,4-triazol-3-yl) methyl]-1,2-dihydro-4H-pyrrolo[3,2,1-ij]quinolin-4-one;
   6-(3-bromophenyl)-8-[(4-bromophenyl)hydroxy(4-methyl-4H-1,2,4-triazol-3-yl) methyl]-1,2-dihydro-4H-pyrrolo[3,2,1-ij]quinolin-4-one;
   N-[[6-(3-chlorophenyl)-1,2-dihydro-4-oxo-4H-pyrrolo[3,2,1-ij]quinolin-8-yl](4-fluorophenyl)(4-methyl-4H-1,2,4-triazol-3-yl)methyl]- acetamide;
   7-(3-chlorophenyl)-9-[(4-chlorophenyl)methoxy(4-methyl-4H-1,2,4-triazol-3-yl) methyl]-2,3 -dihydro-1H, 5H-benzo[ij]quinolizin-5-one;
   6-(3-chlorophenyl)-8-[(4-fluorophenyl)(2-hydroxyethoxy)(4-methyl-4H-1,2,4-triazol -3-yl)methyl]-1,2-dihydro-4H-pyrrolo[3,2,1-ij]quinolin-4-one;
   6-(3-chlorophenyl)-8-[(4-fluorophenyl)-1H-imidazol-1-yl(4-methyl-4H-1,2,4-triazol -3-yl)methyl]-1,2-dihydro-4H-pyrrolo[3,2,1-ij]quinolin-4-one;
   8-[amino(4-fluorophenyl)(4-methyl-4H-1,2,4-triazol-3-yl)methyl]-6-(3-chlorophenyl )-1,2-dihydro-4H-pyrrolo[3,2,1-ij]quinolin-4-one and pharmaceutically acceptable salts thereof.

4. A pharmaceutical composition comprising a pharmaceutically acceptable carrier and a compound of claim 1.

5. An intermediate of formula (IVa):

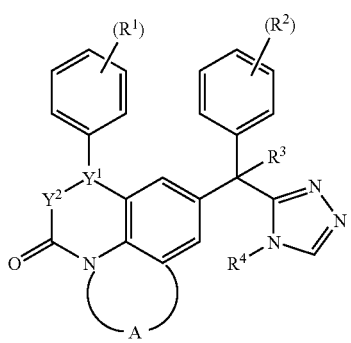

(I)

wherein:
   -A- is a bivalent radical of formula selected from the group consisting of

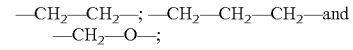

$>Y^1-Y^2-$is$>>C=CR^5$ is hydrogen or halo;
   $R^1$ is selected from the group consisting of hydrogen or halo;
   $R^2$ is selected from the group consisting of hydrogen, halo, or cyano;
   $R^4$ is $C_{1-6}$alkyl, and $R^{21}$ is hydrogen or $C_{1-6}$alkyl.

* * * * *